(12) United States Patent
Zaia et al.

(10) Patent No.: US 6,511,662 B1
(45) Date of Patent: Jan. 28, 2003

(54) TREATMENT OF CYTOMEGALOVIRUS USING AMINOPEPTIDASE N

(75) Inventors: John A. Zaia, Arcadia; Terrence D. Giugni, Alta Loma, both of CA (US); Erna Moller, Morabergsv 14, 13333 Saltsjobaden; Cecilia Söderberg, Hagersten, both of (SE)

(73) Assignees: Erna Möller, Saltsjöbaden (SE); Cecilia Söderberg-Nauclér, Hagersten (SE)

( * ) Notice: Subject to any disclaimer, the term of this patent is extended or adjusted under 35 U.S.C. 154(b) by 0 days.

(21) Appl. No.: 09/722,376

(22) Filed: Nov. 28, 2000

Related U.S. Application Data

(60) Division of application No. 08/099,664, filed on Jul. 30, 1993, now abandoned, which is a continuation-in-part of application No. 08/006,982, filed on Jan. 21, 1993, now abandoned.

(51) Int. Cl.[7] ............................................. A61K 38/48
(52) U.S. Cl. ................................... 424/94.67
(58) Field of Search ...................... 424/94.67

(56) References Cited

PUBLICATIONS

Sörberg et al., "In Situ Hybridization and Immunofluorescence Methods for Identification of CMV Encoded RNA and Antigens . . . ," 17th International Herpes Virus Workshop, Edinburgh, Scotland, Aug. 1–7, 1992, p. 222.

Bowden et al., "A Comparison of Filtered leukocyte–Reduced and Cytomegalovirus (CMV) Seronegative Blood Products . . . ," *Blood*, 86(9):3598–3603, 1995 (Abstract).

Dumont et al., "The Effect of leukoycyte–Reduction Method on the Amount of Human Cytomegalovirus in Blood Products . . . ," *Blood*, 97(11):3640–3647, 2001 (Abstract).

Soderberg, C. et al., "Identification of Blood Mononuclear Cells Permissive of Cytomegalovirus Infection in Vitro," *Transpl. Proc.*, 25(1):1416–1418, 1993.

Soderberg, C. et al., "Definition of a Subset of Human Peripheral Blood Mononuclear Cells that are Permissive in Human Cytomegalovirus Infection," *J. Virol.* 67(6):3166–3175, 1993.

Look, A. T. et al., "Human Myeloid Plasma Membrane Glycoprotein CD13 (gp150) is Identical to Aminopeptidase N," *J. Clin. Invest.*, 83:1299–1307, 1989.

Noren, O. et al., "Molecular and Cellular Basis of Digestion," *Elsevier Biomedical Press*, Amsterdam, p. 324–325, 1986, ix–xix.

Vallee, B. L. et al., "Zinc Coordination, Function, and Structure of Zinc Enzymes and Other Proteins," *Biochemistry*, 29(24):5647–5659, 1990.

Robert H. Rubin, M.D., "Preemptive Therapy in Immunocompromised Hosts," *N. Engl. J. Med.*, 324(15):1057–1059, 1991.

Ashmun, R. A. et al., "Deletion of the Zinc–Binding Motif of CD13/Aminopeptidase N Molecules Results in Loss of Epitopes that Mediate Binding of Inhibitory Antibodies," *Blood*, 79(12):3344–3349, 1992.

Spaete, R. R. et al., "Insertion and Deletion Mutagenesis of the Human Cytomegalovirus Genome," *Proc. Natl. Acad. Sci. USA*, 84:7213–7217, 1987.

The Merck Manual of Diagnosis and Therapy, Merck Research Laboratories, Rahway, NJ 1992; pp. 204–205.

*Primary Examiner*—Jean C. Witz
(74) *Attorney, Agent, or Firm*—Rothwell, Figg, Ernst & Manbeck

(57) ABSTRACT

A method for the prevention or treatment of human cytomegalovirus is described. Aminopeptidases, preferably in soluble form is administered exogenously to the patient. The invention involves the discovery that aminopeptidases are a CMV surface protein involved in post-binding events in the CMV infection process. The invention includes the discovery that AP, including specifically APN, on the surface of the virion and on the surface of the cell is involved in the CMV infection process.

5 Claims, 3 Drawing Sheets

TREATMENT OF CYTOMEGALOVIRUS USING AMINOPEPTIDASE N

This application is a divisional of U.S. patent application Ser. No. 08/099,664, filed Jul. 30, 1993, abandoned, which is a continuation-in-part of U.S. patent application Ser. No. 08/006,982 filed Jan. 21, 1993 abandoned.

TECHNICAL FIELD

This invention relates to the use of aminopeptidases (AP), preferably human aminopeptidase N (APN), for the prevention and treatment of human cytomegalovirus (CMV).

BACKGROUND OF THE INVENTION

Human cytomegalovirus is responsible for significant morbidity and mortality in the immunocompromised groups, i.e., neonates, organ transplant recipients, AIDS patients (1–3).* Treatment is limited because the early events of CMV infection, involving cell binding and penetration, are largely unknown (4). At least four different cell surface proteins, a 30–34 K protein(s) (5–7), a 92.5 K protein (8), a heparin-binding protein (9), and class I human leukocyte antigen (10), have been suggested as important in virus binding.

* A bibliography precedes the claims.

It has recently been reported that CD13 (human aminopeptidase N, APN) is expressed on blood cells susceptible in vitro to HCMV infection (11, 12, 13).

APN is a metalloprotease present on apical surfaces of epithelial cells (14–17). It has been reported to be a binding protein for certain coronaviruses (18, 19).

CD4 is a T-cell receptor for the HIV virion surface glycoprotein gp 120 which also migrates to the surface of HIV infected cells. Soluble forms of CD4 have been developed for circulation in the blood to bind both HIV and infected T-cells and thus prevent the virus from infecting new T-cells. See, e.g., Research News, 1559–1560 (1989).

SUMMARY OF THE INVENTION

It has been discovered that AP, including aminopeptidase N and fragments thereof, are important in CMV infection. It is surprisingly present both on CMV virions and on the cell surface and mediates critical event(s) of infection. Another aspect of the invention includes neutralization or mediation of CMV infection by the use of an AP antibody to remove CMV from blood products and from bone marrow by binding to the virions. Bone marrow transplant (BMT) recipients may receive marrow or blood products which have been purged by treatment with free or immobilized antibody to AP or water soluble AP (SAP) linked to a solid support to remove both CMV virions and cells which are susceptible to and thus may harbor and transmit CMV infection. Such cells form a relatively small sub-population and may eventually be replaced by differentiation of healthy stem cells.

An important aspect of the invention is the discovery that sAP inhibits or neutralizes CMV infection. sAP thus functions as an antiviral agent. Pursuant to this aspect of the invention, sAPN or truncated forms thereof which contain the domain which mediates infection after CMV is bound to the cell are administered exogenously to a patient or expressed as a polypeptide in the cells of a CMV patient. In like manner, APN or truncated forms thereof may be administered prophylactically prior to infection. For example, AP preemptive therapy is provided for management of patient populations such as AIDS patients, bone marrow transplant or organ transplant recipients at risk for CMV disease. The procedure is similar to that previously used for ganciclovir (20).

The invention also includes the administration of antibodies to aminopeptidases and the administration of enzyme inhibitors of aminopeptidase. Further, combinations of an aminopeptidase and an antibody thereto or an enzyme inhibitor thereof are contemplated.

Figure 1A:
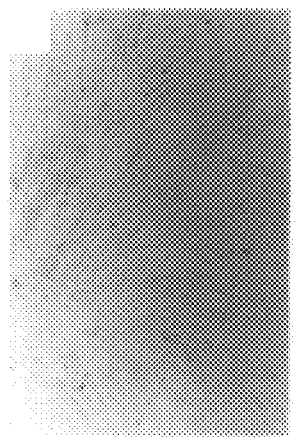
FIG. 1. Inhibition of CMV Towne-strain (RC256) infection of HL734 cells by U71, an APN specific monoclonal antibody. HL734 cells were uninfected (a) or infected with CMV RC256 strain encoding the bacterial β-galactosidase gene in the absence (b) or presence of an APN specific antibody (c), control mouse ascites (d) or a polyclonal antibody to the epidermal growth factor-receptor (a).
Figure 1B:
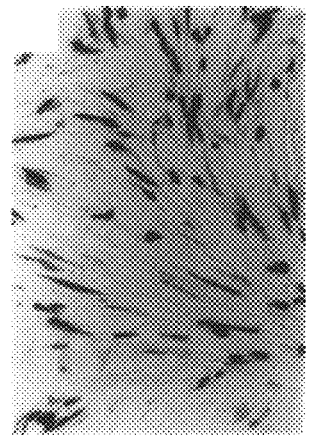
Figure 1C:
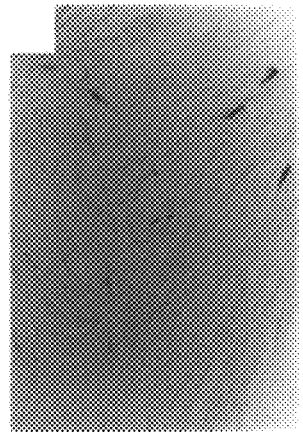
Figure 1D:
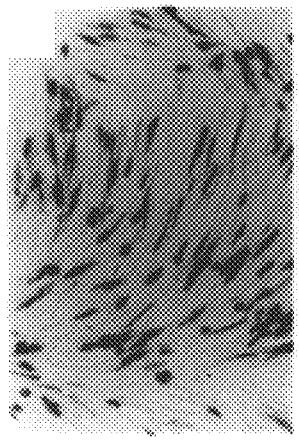
Figure 1E:
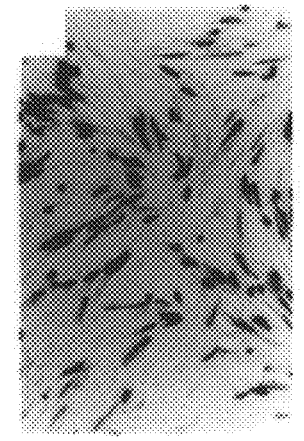

Methods. Human embryonic lung fibroblasts (HL734) grows in 96-well plates were infected with CMV RC256 in the absence or presence of various antibodies. Cells were incubated with RC256 at MOI=1 for 2 hours at 4° C., washed, and incubated at 37° C. for 16 hours. The cells were fixed in 1% phosphate-buffered glutaraldehyde for 15 minutes, washed, and assayed for the expression of β-galactosidase by incubation with Bluo-Gal (430 µg/ml) (Gibco/BRL) for 16 hours at 37° C. An APN-specific antibody (U71), control mouse ascites or a rabbit anti-human epidermal growth factor-receptor serum were added during incubation of cells with virus. Infected cells were detected by the presence of precipitated blue substrate in cytoplasm of cells as visualized by light microscopy.

FIG. 2. Ability to inhibit infection by compounds that interact with human aminopeptidase N. Panel a: HL734 cells were infected with CMV strain RC256 in the presence of serial dilutions of either U71 (■) or control mouse ascites ([ ]). Infection was quantitatively determined by spectrophotometric measurement of the cleavage of p-nitrophenyl-β-D-galactopyranoside by β-gal. Panel b: HL734 were infected with CMV strain AD169 (■) or Semliki Forest Virus (SFV) ([ ]) in the presence of increasing concentration of bestatin. Infection was quantitatively determined by immunocytochemistry using an antibody to the mIE protein of CMV or immune serum to SFV and enumeration of infected calls. Panel c: the binding of $^{35}$S-HCMV to MRC-5 cells in the presence of mouse IgG (X) or antibody to APN (○). Panel d: the aminopeptidase N activity on the surface of HL734 (■), NIH-3T3 (○), hAPN-3T3 ([ ]), or hAPNmut-3T3 (Δ) cells expressed as optical density of reaction product p-nitroanilide.

Method. Infection of HL734 with CMV RC256 was performed as described in FIG. 1 in the presence of serial dilutions of either UT71 or a control mouse ascites. Cells were washed, fixed with glutaraldhyde and assayed for β-gal expression by incubation with p-nitrophenyl-β-D-galactopyranoside (1 mg/ml) and the production of p-nitrophenol was measured spectrophotometrically at 410 nm. To measure the effect of aminopeptidase inhibitors on viral infection, HL734 were preincubated with increasing concentrations of bestatin for 1 hour at 37° C., infected with CMV strain AD169 at an MOI=1–10 or SFV at an MOI=30 for 1 hour at 37° C., washed, and incubated in fresh media for six hours at 37° C. After fixation in ice cold acetone/methanol (1/1), CMV nuclear antigens were detected with a mouse monoclonal to the 72K CMV mIE protein (NEW/Dupont, Inc.) followed by a phycoerythrine-labelled F(ab')$_2$ fragment of rabbit-anti mouse IgG Dakopatts, Inc). Cells infected with SFV were demonstrated using a rabbit polyclonal immune serum against SFV followed by a rhodamine-conjugated goat anti-rabbit IgG (Biosystems, Inc.). Binding of HCMV to MRC-5 cells was carried out by incubating increasing concentration of $^{35}$S-HCMV with MRC-5 cells for 2 hours at 4° C. Incubation was carried out in the presence of mouse IgG (Sigma, Inc.) or anti-leuM7 (Becton Dickinson, Inc.) at a concentration of 16 µg/ml. Cells were washed five times with hepes-buffered saline, solubilized with 0.5 M NaOH, and cell-associated $^{35}$S-labelled virions was measured quantitatively by liquid scintillation counting. Aminopeptidase activity on intact cells was measured by plating 1–5×104 cells in 96-well plates, incubating overnight in fresh media, and the washed and incubated with alanine-p-nitroanilide (6 mM) at 37° C. At various times, the free p-nitroanilide released was measured spectrophoto-metrically at 410 nm. The aminopeptidase activity was normalized to cell number measured by BCA protein assay (Pierce). All measurements were determined in triplicate.

FIG. 3. Susceptibility to in vitro CMV infection of human fibroblasts and mouse cells expressing human APN. Parental murine NIH-3T3 cells (panels a and b), transfected NIH-3T3 cells expressing high levels of native human APN (hAPN-3T3) (panels c and d) or mutant human APN (hAPNMUT-3T3; 15,21) which lacks 39 amino acids at positions 360–399 including the zinc-binding site at positions 388–392 necessary for enzyme activity (panels e and f), and human HL734 (panels g and h) were uninfected (panels a, c, e and g) or infected (panels b, d, f and h) with CMV RC256. Infection was performed and assayed as described in the legend to FIG. 1.

DETAILED DESCRIPTION OF THE INVENTION

This invention relates to the involvement of aminopeptidases in human CMV infection. Antibodies to APE not only inhibit infection, but also block binding of CMV virions to susceptible cells by binding to and thus blocking CMV virions. compounds which inhibit aminopeptidase activity completely block CMV infection. CMV-resistant murine fibroblasts became susceptible to CMV infection after transfection with complementary DNA encoding human APN. However, murine fibroblasts transfected with mutant APN, lacking the enzymatic domain, remain susceptible to CMV infection. Thus, APN appears to mediate CMV infection but its enzymatic domain is not necessary for infection.

To investigate the role that APN plays in the early interaction of CMV with human fibroblasts, cell strains HL734 and MRC-5 were exposed to virus in the presence of APN-specific monoclonal antibodies U71, U81, WM47, or anti-Leu M7. As shown in FIG. 1, U71 protected HL734 from infection with CMV RC256, a recombinant form of CMV Towne strain that encodes the β-galactosidase (β-gal)-gene linked to a CMV early promoter (22). No protection was observed in cells treated with control mouse ascites, mouse IqG or with antibodies directed against the epidermal growth factor-receptor (anti-EGFR) known to be present on the surface of these fibroblasts. The dose response curve of CMV inhibition by U71 indicated that inhibition was directly proportional to the amount of anti-APN antibody used (see FIG. 2a). Similarly, U81, WM47, and anti-Leu M7 all inhibited CMV infection in a dose-dependent fashion. U81 and U71 inhibited infection to a greater extent than anti-Leu M7 or WM47. See Table 1.

TABLE 1

Effect of anti-APN monoclonal antibodies and aminopeptidase inhibitors on CMV infection

|  | Inhibition of CMV Infection[a] | Inhibition of SFV Infection[b] | Inhibition of aminopeptidase activity[c] |
|---|---|---|---|
| Monoclonal antibodies[d] |  |  |  |
| U71 | + | ND[e] | + |
| U81 | + | ND | + |
| WM47 | + | – | – |
| anti-Leu M7 | + | – | – |
| Chemical inhibitors[d] |  |  |  |
| actinonin | + (3.3) | – | + |
| bestatin | + (2.5) | – | + |
| 1,10-phenanthroline | + (0.25) | – | + |
| 2,2'-dipyridyl | + (2.8) | – | + |

[a]The inhibition of CMV infection was determined as described in the description of FIG. 2.
[b]The inhibition of Semliki Forest Virus (SFV) infection was determined as described in the description of FIG. 2.
[c]The inhibition of enzymatic activity was measured using the substrate alanine-p-nitroanilide as described in the description of FIG. 2.
[d]Chemical inhibitors were tested at the concentrations that gave maximum inhibition without toxicity to the cells: actinonin, 5.45 mM; bestatin, 4.35 mM; 1,10-phenanthroline, 0.45 mM; 2,2'-dipyridyl, 3.74 mM. The 50% inhibitory dose given in millimolar concentration is listed in parenthesis. Antibodies were tested at a concentration that gave maximum effect: U71, 1.8 mg/ml; U81, 2 mg/ml; WM47, 20 ug/ml; anti-LeuM7, 3.7 ug/ml. + = >50 inhibition compared to mouse IgG control; – = no inhibition.
[e]ND = not done.

[a] The inhibition of CMV infection was determined as described in the description of FIG. 2.
[b] The inhibition of Semliki Forest Virus (SFV) infection was determined as described in the description of FIG. 2.
[c] The inhibition of enzymatic activity was measured using the substrate alanine-p-nitroanilide as described in the description of FIG. 2.
[d] Chemical inhibitors were tested at the concentrations that gave maximum inhibition without toxicity to the cells: actinonin, 5.45 mM; bestatin, 4.35 mM; 1,10-phenanthroline, 0.45 eM; 2,2'-dipyridyl, 3.74 mM. The 50% inhibitory dose given in millimolar concentration is listed in parenthesis. Antibodies were tested at a concentration that gave maximum effect: U71, 1.8 mg/ml; U81, 2 mg/ml; WM47, 20 ug/ml; anti-LeuM7, 3.7 ug/ml. +=>50 inhibition compared to mouse IgG control; –=no inhibition.
[e] ND=not done.

Figure 2A:
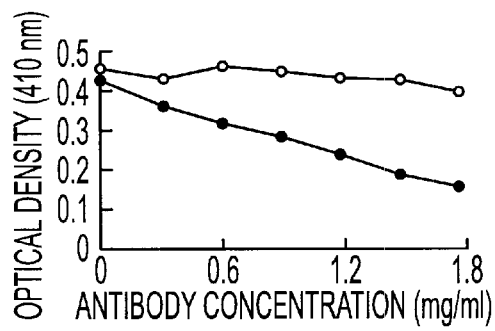
Figure 2B:
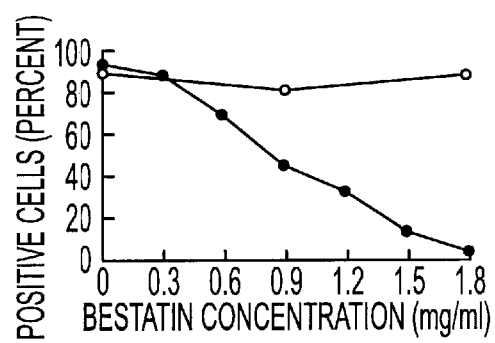

To investigate whether the enzymatic activity of APN is necessary for CMV infection, four different aminopeptidase inhibitors, actinonin, bestatin, 2,2'-dipyridyl and 1,10-phenanthroline, were evaluated for their effect on enzymatic activity and CMV infection bestatin and actinonin are competitive inhibitors of arinoneptidases, ard 1,10-phenanthroline and 2,2'-dipyridyl inhibit aminopeptidase activity by chelating zinc required for enzyme function. These compounds were used at concentrations which were demonstrated to inhibit APN in cells using alanine-p-nitronailide as substrate (see Table 1). Toxicity of these substances, measured by trypan blue uptake in cells treated with the inhibitors, was less than 10% in the highest concentrations used (data not shown). As shown in FIG. 2b, bestatin inhibited CMV infection at a 50% inhibitory concentration of 2.5 mM. As shown in Table 1, actinonin, 1,10-phenanthroline and 2,3'-dipyridyl inhibited CMV infection with 50% inhibition doses of 3.3, 0.25, and 2.8 mM, respectively, further suggesting that APN is involved in CMV infection.

Figure 2C:
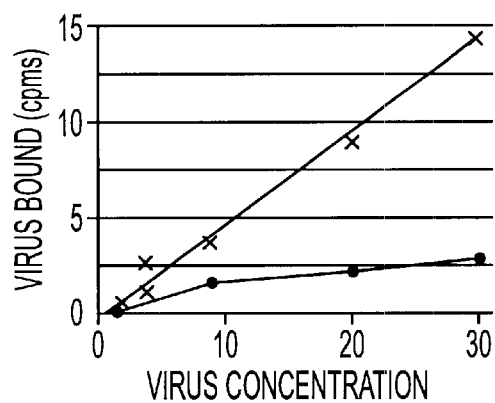
Figure 2D:
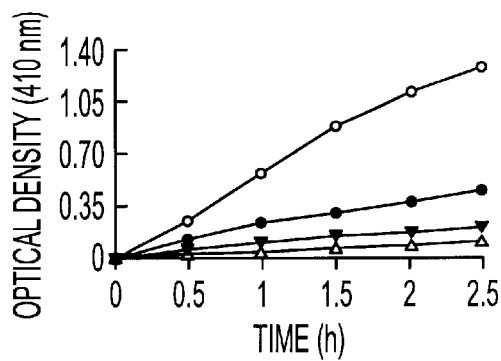

The effect of APN-specific antibodies on binding of $^{35}$S-labeled CMV virions to MRC-5 cells was analyzed. Incubation of cells with increasing concentration of virions resulted in increased binding of CMV to the cells (see FIG. 2c). If binding was done in the presence of control mouse IgG, there was no effect on binding (FIG. 2c). However, binding in the presence of APN-specific antibodies (anti-LeuM7) resulted in a decrease in CMV binding (see FIG. 2c).

To further investigate the importance of APN and its enzymatic activity during CMV infection, murine cells (NTH-3T3) were transfected with DNA for hAPN (hAPN-3T3) or for a truncated form of the protein lacking 39 amino acids from a region containing the active site (hAPMUT-3T3). The presence of surface hAPN was confirmed on the human cells and on the transfected NIH-3T3 cells by flow cytometric analyses using APN-specific monoclonal antibodies (data not shown). To confirm the level of APN activity in these cells, they were tested for ability to cleave aminopeptidase substrate alanine-p-nitroanilide. Enzymatic activity was present in the hAPN-3T3 and HL734 cells but not in the parent NIH-3T3 or in hAPMUT-3T3 cells (see FIG. 2d). All cells were then challenged with CMV RC256, β-gal, the marker for virus infection, was observed on a greater number of the cells which expressed hAPN (see FIG. 3). Parental cells showed little or no expression of CMV encoded genes compared to the APN-expressing cells (compare FIGS. 3b and 3d/3f). Similarly, when evaluated for expression of the 72K major immediate early (mIE) protein of CMV, there was greatly enhanced expression in the transfected cells (data not shown). Thus, expression of hAPN on murine cells permits infection of the cells by HCMV. Importantly, virus infection was observed in a greater number of cells expressing the truncated form of APN than in those with unmodified hAPN. (See Table 2) Infection of these cells expressing the truncated form of hAPN with CMV resulted in a 50-fold increase of CMV-infected cells compared to the hAPN-nonexpressing NIH 3T3 cells which is a 5-fold increase over cells transfected with native hAPN.

TABLE 2

HCMV gene expression in murine cell transfectants

|  |  | HL734 | NIH-3T3 | hAPN-3T3 | hAPNMUT-3T3 |
|---|---|---|---|---|---|
| mIE expression[a] percent | d1 | 19 | <0.25 | 1.7 | 7.6 |
|  | d3 | 25 | <0.25 | 2.5 | 10 |
|  | d7 | 90 | <0.25 | 2.4 | 13 |

[a]Percent cells expressing the 72-kDa mIE antigen of HCMV were determined 1, 3 or 7 days postinfection with AD169. Monolayers of HL734 cells were inoculated at MOI = 1–10 for 2 hours at 4° C., washed and incubated in fresh media. At day 1, 3 and 7 postinfection, the cells were fixed and assayed for the expression of HCMV mIE antigen. The expression of mIE nuclear antigen was detected after fixation in ethanol/acetone by incubation with a mouse monoclonal directed against the 72-kDa HCMV mIE protein (NEN-DuPont, Boston, MA or Biosoft, Paris, France) followed by a FITC-labelled (F(ab$^1$)$_2$ fragment of rabbit-anti mouse IgG (Dakopatts). Infected cells were detected by using a Nikon microscope fitted with epi-illumination optics. The number of HCMV-antigen positive cells were counted and presented as percent of total cells.

[a] Percent cells expressing the 72-kDa mIE antigen of HMCV were determined 1, 3 or 7 days postinfection with AD169. Monolayers of HL734 cells were inoculated at MOI=1–10 for 2 hours at 4° C., washed and incubated in fresh media. At day 1, 3 and 7 postinfection, the cells were fixed and assayed for the expression of HCMV mIE antigen. The expression of mIE nuclear antigen was detected after fixation in ethanol/acetone by incubation with a mouse monoclonal directed against the 72-kDa HClC mIE protein (NEN-Dupont, Boston, Mass. or Biosoft, Paris, France) followed by a FITC-labelled (F(ab')$_2$ fragment of rabbit-anti mouse IgG (Dakopatts). Infected cells were detected by using a Nikon microscope fitted with epi-illumination optics. The number of HCMV-antigen positive cells were counted and presented as percent of total cells.

Figure 3A:
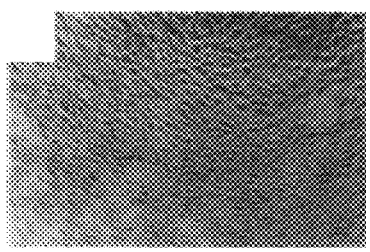
Figure 3B:
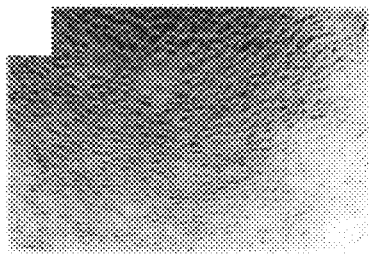
Figure 3C:
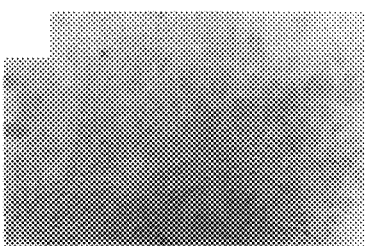
Figure 3D:
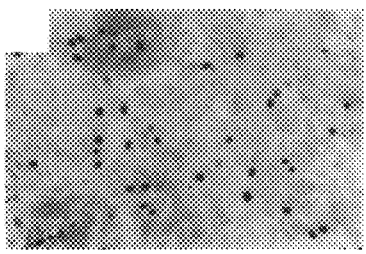
Figure 3E:
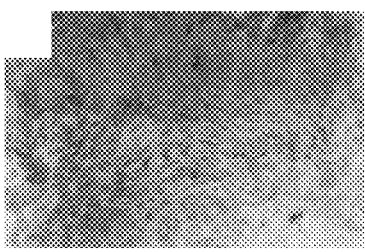
Figure 3F:
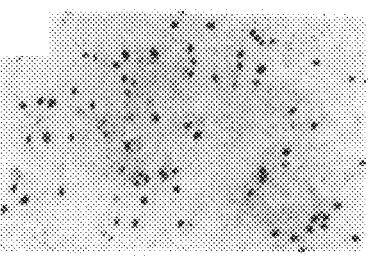
Figure 3G:
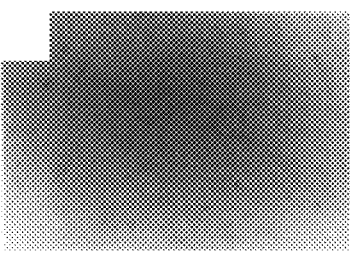
Figure 3H:
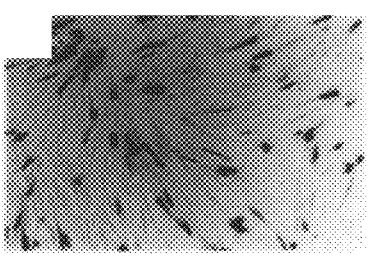

These results suggest that the enzymatic activity of this molecule is not essential for infection and that the truncated form of APN expressed in the hAPN-mut 3T3 cells enhances a cells susceptibility to CMV infection to a greater extent than the native form (compare FIGS. 3d and 3f and see Table 3).

The mutant form of hAPN, hAPNmut-3T3, was obtained as follows. The full length human hAPN cDNA subcloned in the pBluescript plasmid was digested with the BstEII restriction endonuclease, which excised an internal 117 base pair (bp) restriction fragment from the cDNA, but did not cut elsewhere in the DNA or in the vector. The deleted fragment of 39 amino acids (positions 360–399 included the coding sequence for the zinc binding motif (HExxH) at amino acid positions (388–392) known to be necessary for the enzymatic activity. DNA, lacking the deleted sequences, was religated correctly and transfected into NIH 3T3 cells by calcium-phosphate precipitation (21). The presence of hAPN on the cell surface was confirmed by immunostaining by monoclonal antibodies and flow cytometric analysis.

The invention this particularly comprises the use in the method of the invention of an aminopeptidase which lacks the site responsible for aminopeptidase activity while retaining HCMV binding activity. Thus, human aminopeptidase N lacking at least the amino acids at positions 388 to 392, may be used, more particularly human aminopeptidase N lacking the amino acids at positions 360 to 399.

These experiments have shown that CMV infection of fibroblasts, as well as binding of virions to these cells, can be inhibited by different monoclonal antibodies directed against APN as well as by inhibitors of APN activity. However, certain of these APN-specific monoclonal antibodies do not inhibit hAPN activity. Furthermore, enhanced CMV infection occurred in murine cells expressing hAPN and in cells in which the enzymatic site had beer, deleted as compared to the parental mouse cells. It appears the, that the enzymatic active site is not essential either for anti-APN inhibition of CMV infection or for the infection of APN-expressing murine cells. The APN-inhibiting compounds which blocked infection may act by changing the conformation of the APN molecule, and thus altering a region which is important for infection. These data suggest that a non-enzyme domain of APN is important for CMV infection of fibroblasts.

Soluble AP is preferred for use in the practice of this invention and may be prepared in known manner. For example, soluble aminopeptidase N are obtained by purification from mouse cells expressing human APN. This may be done by a modification of the methodology of Danielsen and Cowell (Danielsen, E. M. and Cowell, G. M. *J. Biochem. Biophys. Methods* 8: 41–47 (1983)).

Peptides corresponding to various domains of human APN are derived by (1) proteolytic digests of soluble hAPN followed by HPLC purification of the peptides, (2) expression in *E. coli*, by recombinant DNA methodologies of various regions of hAPN. These *E. coli* expressed peptides may be purified by HPLC, and (3) synthesis of synthetic peptides.

Table 3 demonstrates that soluble porcine-leucine aminopeptidases block CMV infection in vitro.

TABLE 3

| Ability of Soluble Aminopeptidases to block CMV Infection[a] | | |
|---|---|---|
| Concentration | Cytosolic PAP[b] | Microsomal PAP[c] |
| 10 ug/ml | 100 | 100% |
| 100 ug/ml | 80 | 80% |

TABLE 3-continued Ability of Soluble Aminopeptidases to block CMV Infection[a]

| Concentration | Cytosolic PAP[b] | Microsomal PAP[c] |
|---|---|---|
| 586 ug/ml | ND[d] | 15% |
| 1000 ug/ml | <10% | ND |

[a]MRC-5 cells, plated in 96 well plates were infected with RC256 in the absence or presence of soluble porcine aminopeptidases (RAP). Cells ware incubated with virus plus PAP for two hours at 4° C., washed and incubated 18 hours with fresh media at 37° C. Cells were fixed with 1% glutaraldehyde and assayed for expression of β-galactosidase by incubation with Blue-Gal (430 ug/ml) for 16 hours at 37° C. Infected cells were detected by presence of precipitated blue substrate observed by light microscopy. The number of cells infected under each condition was normalized to cells infected in absence of any aminopeptidase.
[b]Cytosolic PAP = cytosolic porcine leucine aminopeptidase obtained from Sigma Chemical Co., Inc. (Catalogue No. L-9875).
[c]Microsomal PAP = microsomal porcine leucine aminopeptidase obtained from Sigma Chemical Co., Inc. (Catalogue No. L-5006).
[d]ND = not done.

[a] MRC-5 cells, plated in 96 well plates were infected with RC256 in the absence or presence of soluble porcine aminopeptidases (RAP). Cells ware incubated with virus plus PAP for two hours at 4° C., washed and incubated 18 hours with fresh media at 37° C. Cells were fixed with 1% glutaraldehyde and assayed for expression of β-galactosidase by incubation with Blue-Gal (430 ug/ml) for 16 hours at 37° C. Infected cells were detected by presence of precipitated blue substrate observed by light microscopy. The number of cells infected under each condition was normalized to cells infected in absence of any aninopeptidase.
[b] Cytosolic PAP=cytosolic porcine leucine aminopeptidase obtained from Sigma Chemical Co., Inc. (Catalogue No. L-9875).
[c] Microsonal PAP=microsomal porcine leucine aminopeptidase obtained from Sigma Chemical Co., Inc. (Catalogue No. L-5006).
[d] ND=not done.

As Table 3 shows, sAPN is an antiviral agent useful for the prevention or treatment of CMV associated diseases.

It has also been determined that preincubation of cells with antibodies to hAPN followed by excessive washing does not block CMV infection, whereas preincubation of the virus with antibodies to hAPN, but not antibodies directed toward other cell surface markers, does block infection. Further, hAPN negative human cells can be infected with CMV and the infection blocked with antibody to hAPN. This suggests that hAPN is not a simple receptor for CMV as suggested by Soderberg, et al. (11–13) and, at least in part, the hAPN on the surface of the virion is, important for CMV infection. However, as indicated by the expression of hAPN in mouse cells and the effect of sAP on CMV infection in fibroblasts, cell associated aminopeptidases play an important role in CMV infection.

BIBLIOGRAPHY

1. Zaia, J. A., et al., *Hematology/Oncology Clinics N.A.* 4: 603–623 (1990).
2. Rubin, R. H., et al., *Transplantation* 24: 458–464 (1977).
3. Jacobson, M. A., et al., *Ann. Intern. Med.* 108: 585–594 (1988).
4. Griffiths, P. D., et al., *Biochemistry* 241; 313–325 (1987).
5. Taylor, H. P., et al., *J. Virol* 63: 3991–3098 (1990).
6. Addish, J. D., et al., *Virology* 176: 337–345 (19).
7. Nowlin, D. M., et al., *J. Virol* 65: 3114–3121 (1991).
8. Kaay, S., et al., *Proc. Natl. Acad. Sci. USA* 86: 10100–10103 (1989).
9. Kari, B. et al., *J. Virol.* 66: 1761–1764 (1992).
10. Grindy, D. E., et al., *Gen. Virol.* 68: 793–803 (1987).
11. Soderberg, C. et al., *Transpl. Proc.* 25: 1416–1418 (1993).
12. Soderberg, C. et al., p. 222, 17th International Herpes Virus Workshop, Edinburgh, Scotland, Aug. 1–7, (1992).
13 . Soderberg, C. et al., *J. Virol.* 67: 3166–3175 (1993).
14. Kenny, A. J. et al.; In Kenny, A. J. and Turner, A. J. (eds.) *Mammalian Ectoenzymes*, Elsevier Scientific Publishing Co., New York, p. 169, (1987).
15. Look, A. T. et al., *J. Clin. Invest.* 83: 1299–1307, (1989).
16. Noren, O. et al., In P. Desnuelle (ed) *Molecular and Cellular Basis of Digestion*, Elsevier/North Holland Biomedical Press, Amsterdam, p. 325, (1986).
17. Vallee, B. L. and Auld, D. S. *Biochemistry* 29: 5647–5659, (1990).
18. Delmas, B. et al., *Nature* 357: 417–420, (1992).
19. Yeager, C. L. et al., *Nature* 357: 420–422, (1992).
20. Schmidt, G. M., et al., *N. Engl. J. Med.* 3.24: 1057–1059 (1991).
21. Ashmun, R. A. et al., *Blood* 79: 3344–3349, (1992).
22. Spaete, R. R. et al., *Proc. Natl. Acad. Sci. USA* 84: 7213–7217, (1987).

What is claimed is:

1. A method for the selective removal of CMV infected cells from blood products or from bone marrow comprising contacting said products or marrow with an antibody to an aminopeptidase.

2. A method as defined by claim 1 in which said aminopeptidase is human aminopeptidase N.

3. A method for the removal of CMV virions from blood products, comprising treating said blood products with an antibody to human aminopeptidase.

4. A method for the selective removal of CMV virions from blood products or from bone marrow comprising contacting said products or marrow with an agent selected from the group consisting of cell-free aminopeptidase and fragments thereof, wherein said agent is linked to a solid support.

5. A method of reducing the interaction of CMV with cells susceptible to CMV infection in a cell sample in need thereof, comprising contacting said cell sample with an agent selected from the group consisting of cell-free aminopeptidase and fragments thereof.

* * * * *